US009133227B2

(12) United States Patent
Azuma et al.

(10) Patent No.: US 9,133,227 B2
(45) Date of Patent: Sep. 15, 2015

(54) PRODUCTION METHODS FOR SOLUBILIZED LIGNIN, SACCHARIDE RAW MATERIAL AND MONOSACCHARIDE RAW MATERIAL, AND SOLUBILIZED LIGNIN

(75) Inventors: Jun-ichi Azuma, Kyoto (JP); Tetsuo Sakamoto, Tokyo (JP); Kiyotaka Onishi, Tokyo (JP)

(73) Assignee: NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 1168 days.

(21) Appl. No.: 12/682,377

(22) PCT Filed: Oct. 15, 2008

(86) PCT No.: PCT/JP2008/002912

§ 371 (c)(1), (2), (4) Date: Apr. 26, 2010

(87) PCT Pub. No.: WO2009/050882

PCT Pub. Date: Apr. 23, 2009

(65) Prior Publication Data

US 2010/0249390 A1 Sep. 30, 2010

(30) Foreign Application Priority Data

Oct. 17, 2007 (JP) ................................ 2007-269704

(51) Int. Cl.
*D21C 1/00* (2006.01)
*C07G 1/00* (2011.01)
*C07H 3/02* (2006.01)

(52) U.S. Cl.
CPC .. *C07G 1/00* (2013.01); *C07H 3/02* (2013.01); *D21C 1/00* (2013.01)

(58) Field of Classification Search
CPC ........................................................ D21C 1/00
USPC .................................... 162/78; 530/500, 507
See application file for complete search history.

(56) References Cited

U.S. PATENT DOCUMENTS 3,671,428 A * 6/1972 Kim .............................. 507/106
4,141,786 A * 2/1979 Eckert ............................ 162/40
4,222,819 A * 9/1980 Fossum et al. .................. 162/76
4,311,553 A * 1/1982 Akerlund et al. ............... 162/23
4,459,174 A * 7/1984 Papageorges et al. .......... 162/40
4,576,609 A * 3/1986 Hageman et al. ................. 8/103
4,622,100 A * 11/1986 Godsay et al. .................. 162/65
5,196,069 A * 3/1993 Cullingford et al. ............ 127/37
5,431,781 A * 7/1995 Walsh ............................ 162/76
5,618,386 A * 4/1997 Arbeloa et al. ................. 162/72
5,641,385 A * 6/1997 Croft et al. ...................... 162/60
5,766,414 A * 6/1998 Alenius et al. .................. 162/52
5,766,415 A * 6/1998 Chen .............................. 162/65
5,853,536 A * 12/1998 Hornsey et al. ................. 162/65
5,858,170 A * 1/1999 Carlsson et al. ................ 162/48
6,555,350 B2 * 4/2003 Ahring et al. ................. 435/162
6,679,972 B1 * 1/2004 Tigerstrom ..................... 162/63
6,743,332 B2 * 6/2004 Haynes et al. .................. 162/78
6,746,568 B1 * 6/2004 Terelius et al. ................. 162/38
7,402,224 B1 * 7/2008 Avignon et al. ................. 162/76
2001/0018956 A1 * 9/2001 Stohrer et al. ................. 162/65
2002/0192774 A1 * 12/2002 Ahring et al. ................ 435/162
2003/0070777 A1 * 4/2003 Ni et al. .......................... 162/24
2003/0168190 A1 * 9/2003 Jokinen et al. .................. 162/63
2007/0031953 A1 * 2/2007 Dunson et al. ................ 435/161
2007/0161095 A1 * 7/2007 Gurin ............................ 435/134
2008/0026431 A1 * 1/2008 Saito et al. .................... 435/105
2008/0105392 A1 * 5/2008 Duggirala et al. .............. 162/23
2009/0053777 A1 * 2/2009 Hennessey et al. ........... 435/101
2010/0006245 A1 * 1/2010 Myllymaki et al. ............ 162/50

FOREIGN PATENT DOCUMENTS

| | | | |
|---|---|---|---|
| CN | 1493577 | A | 5/2004 |
| CN | 101092435 | A | 12/2007 |
| CN | 101230547 | A | 7/2008 |
| EP | 0 141 138 | A1 | 5/1985 |
| JP | 59-204997 | | 11/1984 |
| JP | 60-88191 | | 5/1985 |
| JP | 2006-141244 | A1 | 6/2006 |
| JP | 2007-74992 | A1 | 3/2007 |
| JP | 2007-74993 | A1 | 3/2007 |
| WO | 2006/031175 | A1 | 3/2006 |
| WO | WO 2006/031175 | A1 | 3/2006 |

OTHER PUBLICATIONS

Hasegawa et al., Energy and Fuels, vol. 18, 2004, 755-760.*
Gould et al., Biotechnology and Bioengineering, vol. 26, 1984, 46-52.*
Saeman, Industrial and Engineering Chemistry, vol. 37, 1945, 43-52.*
S. Anwer, et al.; "Delignification of woody biomass by aqueous hydrogen peroxide;" Collection of summaries of the research presentation lectures at the 70th annual convention of the Society of Chemical Engineers, Japan; p. 649, O315; 2005; (2 Sheets.).
International Search Report for International Application No. PCT/JP2008/002912 dated Dec. 26, 2008.
Chinese Office dated Apr. 25, 2013, in the corresponding Chinese patent application No. 200880111884.0.
Supplementary European Search Report dated Mar. 29, 2012, in counterpart European Application No. EP 08840157.

* cited by examiner

*Primary Examiner* — Liam J Heincer
(74) *Attorney, Agent, or Firm* — Kratz, Quintos & Hanson, LLP

(57) ABSTRACT

A new lignin degradation product, a method for producing the same, and methods for producing a saccharide raw material and a monosaccharide raw material are provided.

The method for producing the new lignin degradation product includes: (a first step) mixing 100 parts by mass of a powder, obtained by pulverizing a lignocellulosic raw material and defatting the resulting powder with an organic solvent, with aqueous hydrogen peroxide in an amount of 20 to 400 parts by mass in terms of hydrogen peroxide and heating the mixture for 5 to 120 minutes at a pressure of 0.1 to 1.5 MPa and a temperature of 80 to 200° C. while irradiating the mixture with microwaves; (a second step) separating insoluble matter from the aqueous hydrogen peroxide; (a third step) extracting the insoluble matter with a solvent to produce an extract; and (a fourth step) distilling the solvent away from the extract to yield a solubilized lignin as a residue. Further, a saccharide raw material composed mainly of a polysaccharide or a monosaccharide raw material is obtained by subjecting the liquid portion or the insoluble matter, respectively, obtained in the first step to a predetermined treatment.

4 Claims, No Drawings

PRODUCTION METHODS FOR SOLUBILIZED LIGNIN, SACCHARIDE RAW MATERIAL AND MONOSACCHARIDE RAW MATERIAL, AND SOLUBILIZED LIGNIN

TECHNICAL FIELD

The present invention relates to production methods of a solubilized lignin, a saccharide (carbohydrate) raw material and a monosaccharide raw material, and to a solubilized lignin.

BACKGROUND ART

Lignin is contained in many plants including trees and grass together with cellulose and polysaccharides other than cellulose (generically referred to as hemicellulose). For example, the amount of lignin contained in trees is about 20 to 30% by mass, although it varies depending on the type of a tree. Note that the amount of cellulose contained in trees is about 40 to 50% by mass, and most of the remaining components are hemicellulose.

In plants, these three components are present in a form associated with each other, which is generally called lignocellulose. Hereinafter, these plants comprising lignocellulose may be called lignocellulose as it is or may be called a lignocellulosic raw material.

One of the main applications of a lignocellulosic raw material is a paper product, and fibrous pulp as a raw material of a paper product is prepared from a lignocellulosic raw material such as wood. There are two types of preparation methods of pulp, a method by mechanical crushing and a method by chemical degradation. Lignin is contained in the pulp obtained by the former method, and lignin is removed from the pulp obtained by the latter method.

A paper product produced by using the pulp obtained by the latter chemical degradation has high whiteness and is treated as a high quality paper product. Therefore, in pulp preparation, lignin can be called an undesirable component.

Further, in recent years, various technologies have been studied for utilizing biomass such as wood which is a renewable, organism-derived organic resource unlike fossil fuel resources and the like to obtain bioenergy and a useful organic substance as a measure against energy exhaustion. Development of these technologies has been accelerated with the remarkable progress of biotechnology as a background, and such technology is already entering the stage of practical application.

In this case, of the three lignocellulosic components, two types of polysaccharide raw materials, hemicellulose and cellulose, are considered to be the target for use, because hemicellulose is easily hydrolyzed with an acid and an enzyme, and cellulose is less easily degraded than hemicellulose but dissolves in a specific solvent such as concentrated sulfuric acid or is hydrolyzed by swelling with an alkali followed by treating with a dilute acid. On the other hand, although lignin can be solubilized, for example, with a mixed solution of sodium hydroxide and sodium sulfite or with dioxane or the like, it has undergone significant chemical modification in this process. Therefore, it is difficult to take out lignin in the form as it is present in plants. For this reason, it is considered to be difficult to find a specific target for use of lignin from the viewpoint of biomass utilization.

As a technology for degrading lignin which is difficult to handle, a technology for obtaining a water-soluble organic acid such as gallic acid, oxalic acid or acetic acid by blowing ozone into a lignocellulose suspension to oxidatively degrade the same (refer to Patent Document 1) has recently been disclosed.

Further, a method is disclosed in which, in order to bleach semi-bleached pulp by removing lignin, the pulp is treated by adding 1.2 g of hydrogen peroxide to 100 g of the pulp while irradiating the pulp with microwaves (refer to Patent Document 2). However, since attention is not paid to lignin itself in this case, it is not known what type of product is obtained as a degradation product of lignin.

Patent Document 1: Japanese Patent Laid-Open No. 2006-141244

Patent Document 2: Japanese Patent Laid-Open No. 60-088191

DISCLOSURE OF THE INVENTION

Problems to be Solved by the Invention

The present invention has been made to develop useful applications of lignin no effective utilization method of which has been sufficiently studied as described above. An object of the present invention is to provide a new lignin degradation product and a new method of treating lignocellulose in which the lignin degradation product can be suitably obtained, and to provide a new method of obtaining a saccharide raw material and a monosaccharide raw material from lignocellulose.

Means for Solving the Problems

The present inventors have extensively and intensively studied suitable applications of lignin. Lignin is known to be a starting material for preparation of useful compounds such as vanillic acid, protocatechuate, gallate, 4-hydroxybenzoate, and shikimate. Lignin is also an effective raw material of polyphenols having a bioactive effect.

When lignin is used as a raw material of the above useful components, it is essential to solubilize lignin and subject the solubilized lignin to proper treatment necessary for obtaining the above target components. However, as described above, since the solubilized lignin has undergone significant chemical modification in conventional technology, it is difficult to use it as a raw material for obtaining the target components. On the other hand, a conventional technology for performing slight degradation treatment in which lignin probably undergoes a relatively little chemical modification will be not suitable as a practical treatment method for obtaining the target components because the amount of lignin solubilized is probably only a very small portion of the whole raw material.

For this reason, the present inventors have studied a production method of a solubilized lignin in which lignin undergoes a relatively little chemical modification and the solubilized lignin can be obtained from lignin occurring in lignocellulose in high yield. As a result, the present inventors have found a method of oxidizing lignocellulose with a large amount of hydrogen peroxide solution while irradiating the lignocellulose with microwaves.

The present invention mainly comprises (a first step) mixing 100 parts by mass (on a dry basis) of a powder obtained by pulverizing a lignocellulosic raw material (may be called lignocellulose or a lignocellulosic material) with aqueous hydrogen peroxide in an amount of 20 to 400 parts by mass in terms of hydrogen peroxide and heating the mixture for 5 to 120 minutes at a pressure of 0.1 to 1.5 MPa and a temperature of 80 to 200° C. while irradiating the mixture with microwaves.

The first step produces a mixture of a solubilized lignin which has undergone a relatively little chemical modification, an insoluble lignin, and a portion of polysaccharides in an aqueous hydrogen peroxide containing the remaining portion of polysaccharides, wherein the mixture is separated from the aqueous hydrogen peroxide as insoluble matter.

The production method of a solubilized lignin according to the present invention comprises (a second step) separating the insoluble matter obtained in the first step from the hydrogen peroxide solution; (a third step) extracting the resulting insoluble matter with a solvent to produce an extract; and (a fourth step) distilling the solvent away from the extract to yield a residue.

In these steps, the insoluble matter which is a mixture of the insoluble lignin and the like and the solubilized lignin is extracted with a solvent to allow the solubilized lignin to move to the extract side to be separated from the insoluble lignin and the like, and the solvent is then distilled away from the extract to obtain the solubilized lignin as a residue.

Moreover, the production method of a saccharide raw material according to the present invention comprises (a fifth step) separating insoluble matter obtained in the first step to obtain a liquid portion; and (a sixth step) removing hydrogen peroxide in the resulting liquid portion.

These steps provide a carbohydrate raw material derived from cellulose and hemicellulose, from which the insoluble matter which is a mixture of an insoluble lignin and the like and a solubilized lignin has been suitably removed.

When the solubilized lignin is compared with lignin which is pulverized down to 20 to 30 μm using a mill and extracted with dioxane and which is generally referred to as milled wood lignin (MWL), significant difference of molecular weight is not observed between them. Therefore, it is inferred that the lignin solubilized by microwaves (MW) has undergone only a weak chemical modification to the extent that it will receive through the process of pulverizing. On the other hand, although cellulose remains in an insoluble portion as fiber, a portion thereof is degraded to form polysaccharides which dissolve in an aqueous phase. Further, it has been determined that most of hemicellulose has been degraded and has moved to the aqueous phase as polysaccharides or monosaccharides. Thus, it has been found that, in the MW irradiation system using a large amount of hydrogen peroxide, most of lignin is solubilized but the extent of chemical modification thereof is low, and that cellulose, particularly hemicellulose, is easily degraded.

Moreover, the production method of a monosaccharide raw material according to the present invention comprises (a seventh step) extracting the insoluble matter obtained in the second step with a solvent to produce an extraction residue; and (an eighth step) adding hydrogen peroxide to the resulting extraction residue followed by reirradiation with microwaves, or adding a strong acid to the resulting extraction residue followed by heating, to obtain soluble matter.

These steps provide a monosaccharide raw material from which insoluble lignin has been suitably removed.

Moreover, the solubilized lignin according to the present invention is a solubilized lignin obtained by the production method of a solubilized lignin as described above and has a weight average molecular weight of from 1500 to 8000.

Advantages of the Invention

The production method of a solubilized lignin according to the present invention comprises (a first step) mixing 100 parts by mass (on a dry basis) of a powder obtained by pulverizing a lignocellulosic raw material with aqueous hydrogen peroxide in an amount of 20 to 400 parts by mass in terms of hydrogen peroxide and heating the mixture for 5 to 120 minutes at a pressure of 0.1 to 1.5 MPa and a temperature of 80 to 200° C. while irradiating the mixture with microwaves; then (a second step) separating the resulting insoluble matter from the aqueous hydrogen peroxide; (a third step) extracting the resulting insoluble matter with a solvent to produce an extract; and (a fourth step) distilling the solvent away from the extract to yield a residue. Therefore, it is possible to suitably obtain a solubilized lignin which has undergone a relatively little chemical modification.

Moreover, the production method of a saccharide raw material according to the present invention comprises (a fifth step) separating insoluble matter obtained in the first step to obtain a liquid portion; and (a sixth step) removing hydrogen peroxide in the resulting liquid portion. Moreover, the production method of a monosaccharide raw material according to the present invention comprises (a seventh step) extracting the insoluble matter obtained in the second step with a solvent to produce an extraction residue; and (an eighth step) adding hydrogen peroxide to the resulting extraction residue followed by reirradiation with microwaves, or adding a strong acid to the resulting extraction residue followed by heating, to obtain soluble matter. Therefore, it is possible to suitably obtain carbohydrates (polysaccharides) including monosaccharides from which lignin has been removed.

BEST MODE FOR CARRYING OUT THE INVENTION

An embodiment of the present invention will be described below.

The production method of a solubilized lignin according to the present embodiment comprises a first step of mixing 100 parts by mass (on a dry basis) of a powder obtained by pulverizing a lignocellulosic raw material (may be called lignocellulose or a lignocellulosic material) with aqueous hydrogen peroxide in an amount of 20 to 400 parts by mass in terms of hydrogen peroxide and heating the mixture for 5 to 120 minutes at a pressure of 0.1 to 1.5 MPa and a temperature of 80 to 200° C. while irradiating the mixture with microwaves; a second step of separating insoluble matter obtained in the first step from the aqueous hydrogen peroxide; a third step of extracting the insoluble matter obtained in the second step with a solvent to produce an extract; and a fourth step of distilling the solvent away from the extract obtained in the third step to yield a residue.

Here, the solubilized lignin refers to lignin having a low molecular weight to the extent that it is soluble in water or a highly polar organic solvent.

A lignocellulosic raw material is a material containing lignocellulose as the main component, and examples thereof include agricultural waste such as arbors such as broad-leaved trees and conifers, herbs such as bagasse (a residue left after the extraction of juice from sugar cane) and rice straw, bamboos, and Japanese apricot kernels. The lignocellulosic raw material may be a food residue such as beer sludge as long as it is a material which contains lignocellulose as the main component. The beer sludge refers to a malt residue produced as a by-product by filtration in the brewery process in which beer is produced by adding yeast to wort and fermenting the wort which is obtained by filtering saccharified malt to remove the malt residue.

The lignocellulosic raw material to be used is preferably pulverized beforehand to a particle size of, for example, about 10 mesh or less. However, the particle size of the lignocellulosic raw material is not limited to the above size, but one that is crushed to a proper size may be used.

The part(s) by mass of the powder obtained by pulverizing the lignocellulosic raw material and defatting the resulting powder with an organic solvent refers to that on a dry basis, that is, the amount of a dry powder obtained by drying it in a drying oven until it reaches constant weight at 70° C. However, although the lignocellulosic raw material that has been dried beforehand may be used, it is not limited to the dried one. A lignocellulosic raw material containing water may be used as it is.

Further, when preparing lignin from lignocellulose used as a raw material, an extraction component contained in the lignocellulosic raw material is preferably defatted with an organic solvent because it is similar to lignin in structure. That is, it is preferred to defat the powder obtained by pulverizing a lignocellulosic raw material. However, defatting is not essential. The organic solvent used for defatting is not particularly limited. For example, an ethanol-benzene mixed solvent, an acetone-methanol mixed solvent, a chloroform-methanol mixed solvent, or the like can be used.

A reaction vessel used in the first step may be a proper one as long as it can transmit microwaves or allows internal irradiation and is suitable for the pressure and temperature conditions. The reaction vessel is charged with a predetermined amount of aqueous hydrogen peroxide and a lignocellulosic raw material, and the lignocellulosic raw material is dispersed in the aqueous hydrogen peroxide with stirring. The aqueous hydrogen peroxide having a proper concentration can be used.

The lignocellulosic raw material may be irradiated with microwaves continuously for a predetermined period of time or intermittently a plurality of times, with short irradiation time. A heat source other than the microwaves may be used together with the microwaves as a source of heating.

In order to separate the insoluble matter obtained in the first step from the aqueous hydrogen peroxide, a proper method such as centrifugal separation can be employed. When centrifugal separation is employed, a treatment including repeated addition of water to the insoluble matter followed by centrifugal separation may be suitably performed in order to more positively separate the insoluble matter from the aqueous hydrogen peroxide.

The resulting insoluble matter is a mixture of a solubilized lignin which has undergone a relatively little chemical modification, an insoluble lignin, cellulose, and a portion of hemicellulose, and is separated and fractionated from the remaining portion (liquid portion) that is the aqueous hydrogen peroxide containing carbohydrates.

Examples of the solvent used for solvent extraction of the insoluble matter obtained in the second step to obtain an extract include, but are not limited to, aqueous methanol and aqueous dioxane. An acetone-water mixed solvent can be used more suitably.

The resulting extract contains a solubilized lignin extracted from the insoluble matter and is separated from the residue of the insoluble matter which contains an insoluble lignin, cellulose, and the like.

Further, the solvent is distilled away from the extract by a proper method such as drying the extract to thereby yield the solubilized lignin as a residue.

The solubilized lignin obtained by the production method of the solubilized lignin according to the present embodiment as described above has a reduced molecular weight, and has a weight average molecular weight of 1500 to 8000.

The resulting soluble lignin has high antibacterial and antifungal properties and can be used for agricultural chemicals and the like as an inexpensive antibacterial agent and antifungal agent derived from natural products.

The resulting soluble lignin can also be suitably used as a raw material of vanillic acid, protocatechuate, gallate, 4-hydroxybenzoate, shikimate, and the like, and polyphenols having a bioactive effect, as described above. Further, the resulting soluble lignin can also be used as a caking additive of coal for producing coke from coal. Furthermore, it is also possible to produce carbon fiber by spinning the soluble lignin followed by carbonization and graphitization. That is, the soluble lignin can also be used as a raw material of carbon fiber.

Next, the production method of a saccharide raw material according to the present embodiment comprises (a fifth step) separating insoluble matter obtained in the first step to obtain a liquid portion; and (a sixth step) removing hydrogen peroxide in the resulting liquid portion. The hydrogen peroxide remaining in the liquid portion may be removed, for example, by using a method of freeze-drying the liquid portion or a method of decomposing hydrogen peroxide using manganese dioxide or catalase.

Here, the liquid portion obtained by separating the insoluble matter is suitably a supernatant liquid obtained after settling the insoluble matter, for example, by centrifugal separation. However, the liquid portion is not limited to the supernatant liquid, but it may be the whole liquid (aqueous hydrogen peroxide) excluding the insoluble matter.

Thus, there is obtained a saccharide (carbohydrate) raw material from which the insoluble matter which is a mixture of an insoluble lignin and the like and a solubilized lignin has been suitably removed. Note that the carbohydrate raw material contains not only polysaccharides but also monosaccharides and oligosaccharides which are appropriately produced depending on reaction conditions.

The carbohydrate raw material obtained by the production method of a carbohydrate raw material according to the present embodiment contains useful polysaccharides such as glucose, xylose, and mannose.

Moreover, the production method of a monosaccharide raw material according to the present embodiment comprises (a seventh step) extracting the insoluble matter obtained in the second step with a solvent to produce an extraction residue; and (an eighth step) adding hydrogen peroxide to the resulting extraction residue followed by reirradiation with microwaves, or adding a strong acid to the resulting extraction residue followed by heating, to obtain soluble matter.

Here, the seventh step, which corresponds to the third step, recovers the extraction residue instead of recovering the extract. Examples of the solvent used for solvent extraction of the insoluble matter include, but are not limited to, an acetone-water mixed solvent, hydrous methanol, and hydrous dioxane.

Acid treatment of the extraction residue yields a monosaccharide raw material from which an insoluble lignin has been suitably removed. Here, the monosaccharide raw material means a raw material containing monosaccharides in an amount and in a concentration sufficient for practically or efficiently obtaining monosaccharides by further treating this raw material.

Further, a longer irradiation time of microwaves may allow hemicellulose and cellulose to be converted to monosaccharides. Thus, the yield of monosaccharides can be increased by irradiating the raw material with microwaves for a long time under a predetermined temperature condition in the presence of hydrogen peroxide. For this reason, this production method may be a method of easily producing ethanol from wood biomass.

EXAMPLES

The present invention will be further described with reference to Examples. Note that the present invention is not limited to Examples to be described below.

Example 1

The woody part of beech, a hardwood, was sufficiently dried and ground with a mill. The ground powder was sifted by a 60 to 80 mesh sieve to collect the minus sieve. To 10 g of the powder was added 50 ml of a mixed solvent of ethanol-benzene (1:2), and the resulting mixture was stirred, filtered, and then dried. The resulting dried product in an amount of 2.0 g was put in a TFM (polytetrafluoroethylene containing less than 1% of perfluoropropyl vinyl ether) degradation vessel manufactured by Milestone General K.K. (volume: 50 ml, resisting temperature: 300° C., resisting pressure: 10 MPa). To the degradation vessel was added 30 ml of 10% by mass aqueous hydrogen peroxide, and a magnetic stirrer was set to the vessel, which was then mounted on a monoblock high-pressure segment set and sealed. While stirring the content of the vessel, the operating conditions of microwaves were set at an output of 500 W and a reaction temperature of 160° C. in the control program, and the content was irradiated with microwaves. The preset temperature was reached in about 2 minutes, and the temperature was further held for 5 minutes, and then the microwave irradiation was stopped. As a microwave heating device, MicroSYNTH manufactured by Milestone General K.K. (1000 W, 2.45 GHz) was used.

The reaction vessel was cooled in ice water after completion of heating before it is opened. The resulting suspension in the vessel was moved to a centrifuging tube and centrifuged for 10 minutes at 8,000×g. The resulting supernatant liquid was removed leaving a pellet produced on the bottom. To the pellet remaining in the centrifuging tube was added 10 ml of pure water, and the pellet was sufficiently suspended using a vortex. The resulting suspension was centrifuged again for 10 minutes at 8,000×g to wash the pellet.

The pellet obtained by repeating the washing operation three times was extracted with a 90% acetone-10% water mixed solvent to produce an extract containing a solubilized lignin. The solvent was removed from the extract under reduced pressure, and the resulting residue was dried in a vacuum dryer at room temperature for 24 hours to yield 1.0 g of pasty solubilized lignin.

On the other hand, 7.5 ml of 72% sulfuric acid was added to 0.75 g of a white fibrous material (extraction residue) remaining after extracting the solubilized lignin contained in the pellet with a 90% acetone-10% water mixed solvent. The resulting mixture was stirred at room temperature for two hours and diluted with distilled water so as to provide a concentration of 3 to 4%. The diluted mixture was moved to a sealable vessel, heated at 121° C. for 30 minutes, and separated into a solution portion and an insoluble portion by filtration, thereby obtaining about 300 ml of a solution (A) containing monosaccharides.

Further, manganese dioxide was added to the supernatant liquid removed from the centrifuging tube and the washing liquid of the pellet as described above to decompose residual hydrogen peroxide. Then, the manganese dioxide was removed from the mixture by filtration to obtain about 50 ml of a solution (B) containing carbohydrates as a filtrate. Alternatively, a method of freeze-drying the supernatant liquid and the washing liquid to thereby obtain carbohydrates as a water-absorbing solid may also be used.

The molecular weight of the resulting solubilized lignin was measured using a differential refractometer manufactured by Showa Denko K.K. and an HPLC apparatus manufactured by JASCO Corporation. The results are shown in Table 1.

The pellet after extracting the soluble lignin had a form of a white powder, and the mass percentage thereof was 37.7% of the total mass of the beech powder used as a starting material. The pellet was treated with 72% sulfuric acid, diluted with water to 3 to 4%, and then hydrolyzed. The solution (A) containing monosaccharides, which was obtained by removing the insoluble portion from the resulting mixture containing the hydrolyzed pellet, was analyzed by HPLC on a column for sugar analysis (DX-500, column CarbopacPA-1 manufactured by Dionex Corporation). The solution (B) obtained by hydrolysis was also subjected to HPLC analysis in the same manner as the solution (A). In addition, the molecular weight of the main component of the carbohydrate raw material contained in the solution (B) (before hydrolysis) was subjected to HPLC analysis using size exclusion chromatography (YMC-Pack Diol-200). The detected sugar composition and the like are summarized in Table 1.

Example 2

The Japanese red pine was selected as a representative example of softwoods and subjected to the same treatment and analysis as in Example 1. The results are shown in Table 1.

Example 3

Bamboo (grown-up moso bamboo) was ground and subjected to the same treatment and analysis as in Example 1. The results are shown in Table 1.

Example 4

The same treatment and analysis as in Example 1 were conducted, except that bagasse was ground, passed through a 60 to 80 mesh sieve, and defatted; and 30 ml of 10% by mass aqueous hydrogen peroxide was added to 1.0 g of the defatted bagasse powder. The results are shown in Table 2.

Example 5

Rice straw was ground and subjected to the same treatment and analysis as in Example 4. The results are shown in Table 2.

Example 6

The same treatment and analysis as in Example 1 were conducted, except that Japanese apricot kernels (shells in Japanese apricot) were ground and passed through a 60 to 80 mesh sieve; and 20 ml of 10% by mass aqueous hydrogen peroxide was added to 3 g of the resulting powder. The results are shown in Table 2.

Reference Example 1

The woody part of beech was sufficiently dried and ground with a mill. The ground powder was sifted by a 60 to 80 mesh sieve to collect the minus sieve. The collected powder in an amount of 2.5 g was put in a sealable pressure vessel, which was sealed after a magnetic stirrer was added thereto. The temperature of the vessel was increased to 160° C. in an oil bath under stirring and the increased temperature was then maintained for 5 minutes. The suspension was moved to a centrifuging tube for centrifugal separation and centrifuged for 10 minutes at 8,000×g. The resulting supernatant liquid was discarded leaving a pellet on the bottom. To the pellet remaining in the centrifuging tube was added 10 ml of pure water, and the pellet was sufficiently suspended using a vortex. Then, the resulting suspension was centrituged again (for 10 minutes at 8,000×g) to wash the pellet. After repeating this operation three times, liquid extraction of a solubilized lignin contained in the pellet was tried with a 90% acetone-10% water mixed solvent, but the extract was almost not obtained.

To the pellet was added 72% sulfuric acid. The resulting mixture was stirred at room temperature for two hours and then diluted about 40-fold with distilled water. The diluted mixture was moved to a sealable vessel, heated at 121° C. for 30 minutes, and separated into a solution portion and an insoluble portion by centrifugal separation. The solution portion was diluted 10-fold with water and analyzed by HPLC on a column for sugar analysis (DX-500, column CarbopacPA-1 manufactured by Dionex Corporation). The detected sugar composition is shown in Table 1.

Reference Example 2

The Japanese red pine was selected as a representative example of softwoods and subjected to the same treatment and analysis as in Reference Example 1. The results are shown in Table 1.

Reference Example 3

Bamboo (grown-up moso bamboo) was ground and subjected to the same treatment and analysis as in Reference Example 1. The results are shown in Table 1.

TABLE 1

| | Soluble lignin | Solution (A) cellulose, hemicellulose | | | Solution (B) cellulose, hemicellulose | | | |
|---|---|---|---|---|---|---|---|---|
| | yield, % (value based on lignocellulose) and molecular weight | Yield, % (value based on lignocellulose) | Percentage of sugar components after hydrolysis, % | | Yield, % (value based on lignocellulose) | Percentage of sugar components after hydrolysis, % | | Molecular weight of sugar raw materials contained |
| Example 1 | 34.6 | 37.1 | Galactose | 1.7 | 62.3 | Arabinose | 1.3 | 11,000 |
| Beech | 5,000 | | Glucose | 90.9 | | Galactose | 1.0 | (including |
| wood | | | Xylose | 6.5 | | Glucose | 21.8 | oligosaccharides |
| powder | | | Mannose | 0.9 | | Xylose | 70.1 | and monosaccharides) |
| | | | | | | Mannose | 5.7 | |
| Example 2 | 10.4 | 12.3 | Arabinose | 0.3 | 84.4 | Arabinose | 16.3 | 13,000 |
| Japanese | 6,000 | | Glucose | 93.6 | | Glucose | 75.9 | (including |
| red pine | | | Xylose | 2.6 | | Xylose | 1.9 | oligosaccharides |
| wood powder | | | Mannose | 3.5 | | Mannose | 5.9 | and monosaccharides) |
| Example 3 | 19.7 | 37.6 | Arabinose | 1.0 | 60.2 | Arabinose | 4.5 | 11,000 |
| Moso | 7,600 | | Galactose | 0.2 | | Galactose | 0.9 | (including |
| bamboo | | | Glucose | 79.3 | | Glucose | 20.8 | oligosaccharides |
| powder | | | Xylose | 19.5 | | Xylose | 73.8 | and monosaccharides) |
| Reference | 0.2 or | 80.8 | Arabinose | 1.1 | 2.8 | Arabinose | 7.2 | — |
| Example 1 | less | | Rhamnose | 0.8 | | Xylose | 92.8 | |
| Beech | | | Galactose | 1.8 | | | | |
| wood | | | Glucose | 51.3 | | | | |
| powder | | | Xylose | 36.1 | | | | |
| 0.2 or less | | | Mannose | 8.9 | | | | |
| Reference | <1.0 | 74.0 | Arabinose | 3.3 | 2.5 | Arabinose | 0.8 | — |
| Example 2 | | | Galactose | 8.0 | | Galactose | 2.8 | |
| Japanese | | | Glucose | 53.7 | | Glucose | 76.8 | |
| red pine | | | Xylose | 12.0 | | Xylose | 4.7 | |
| wood powder | | | Mannose | 23.7 | | Mannose | 15.0 | |
| Reference | <1.0 | 75.8 | Arabinose | 3.3 | 3.2 | Arabinose | 4.5 | — |
| Example 3 | | | Galactose | 0.9 | | Xylose | 95.5 | |
| Moso | | | Glucose | 49.9 | | | | |
| bamboo powder | | | Xylose | 45.9 | | | | |

TABLE 2

| | Soluble lignin | Solution (A) cellulose, hemicellulose | | | Solution (B) cellulose, hemicellulose | | | |
|---|---|---|---|---|---|---|---|---|
| | yield, % (value based on lignocellulose) and molecular weight | Yield, % (value based on lignocellulose) | Percentage of sugar components after hydrolysis, % | | Yield, % (value based on lignocellulose) | Percentage of sugar components after hydrolysis, % | | Molecular weight of sugar raw materials contained |
| Example 4 | 18.5 | 36.1 | Arabinose | 0.8 | 38.3 | Arabinose | 8.0 | 11,000 |
| Bagasse | 7,000 | | Galactose | 0.2 | | Galactose | 1.4 | (including |
| powder | | | Glucose | 83.3 | | Glucose | 22.0 | oligosaccharides |
| | | | Xylose | 15.7 | | Xylose | 68.7 | and monosaccharides) |
| Example 5 | 16.5 | 42.6 | Arabinose | 2.9 | 26.4 | Arabinose | 13.6 | 10,000 |
| Rice | 4,800 | | Galactose | 0.8 | | Galactose | 2.4 | (including |
| straw | | | Glucose | 75.9 | | Glucose | 36.6 | oligosaccharides |
| powder | | | Xylose | 20.5 | | Xylose | 47.4 | and monosaccharides) |

TABLE 2-continued

| | Soluble lignin | Solution (A) cellulose, hemicellulose | | | Solution (B) cellulose, hemicellulose | | | |
|---|---|---|---|---|---|---|---|---|
| | yield, % (value based on lignocellulose) and molecular weight | Yield, % (value based on lignocellulose) | Percentage of sugar components after hydrolysis, % | | Yield, % (value based on lignocellulose) | Percentage of sugar components after hydrolysis, % | | Molecular weight of sugar raw materials contained |
| Example 6 | 16.5 | 37.4 | Arabinose | 0.6 | 38.8 | Arabinose | 0.9 | 10,000 |
| Japanese | 4,800 | | Rhamnose | 0.4 | | Rhamnose | 1.8 | (including |
| apricot | | | Galactose | 0.9 | | Galactose | 2.6 | oligosaccharides |
| kernel | | | Glucose | 58.8 | | Glucose | 6.5 | and monosaccharides) |
| powder | | | Xylose | 39.3 | | Xylose | 88.2 | |

The invention claimed is:

1. A production method of a solubilized lignin, comprising:

a first step of mixing 100 parts by mass (on a dry basis) of a powder obtained by pulverizing a lignocellulosic raw material with aqueous hydrogen peroxide in an amount of 20 to 400 parts by mass in terms of hydrogen peroxide and heating the mixture for 5 to 120 minutes at a pressure of 0.1 to 1.5 MPa and a temperature of 80 to 200° C. while irradiating the mixture with microwaves;

a second step of separating insoluble matter obtained in the first step from the aqueous hydrogen peroxide;

a third step of extracting the insoluble matter obtained in the second step with a solvent to produce an extract; and a fourth step of distilling the solvent away from the extract obtained in the third step to yield a residue.

2. The production method of a solubilized lignin according to claim 1, wherein the solvent used in the third step is an acetone-water mixed solve.

3. A production method of a saccharide raw material, comprising:

a first step of mixing 100 parts by mass (on a dry basis) of a powder obtained by pulverizing a lignocellulosic raw material with aqueous hydrogen peroxide in an amount of 20 to 400 parts by mass in terms of hydrogen peroxide and heating the mixture for 5 to 120 minutes at a pressure of 0.1 to 1.5 MPa and a temperature of 80 to 200° C. while irradiating the mixture with microwaves;

a second step of separating insoluble matter obtained in the first step to obtain a liquid portion; and a third step of removing hydrogen peroxide in the liquid portion obtained in the second step.

4. A production method of a monosaccharide raw material, comprising:

a. first step of mixing 100 parts by mass (on a dry basis) of a powder obtained by pulverizing a lignocellulosic raw material with aqueous hydrogen peroxide in an amount of 20 to 400 parts by mass in terms of hydrogen peroxide and heating the mixture for 5 to 120 minutes at a pressure of 0.1 to 1.5 MPa and a temperature of 80 to 200° C. while irradiating the mixture with microwaves;

a second step of separating insoluble matter obtained in the first step from the aqueous hydrogen peroxide;

a third step of extracting the insoluble matter obtained in the second step with a solvent to produce an extraction residue; and a fourth step of adding hydrogen peroxide to the extraction residue obtained in the third step followed by reirradiation with microwaves, or adding a strong acid to the extraction residue followed by heating, to obtain soluble matter.

* * * * *